United States Patent
Shakespeare et al.

(10) Patent No.: US 9,266,694 B2
(45) Date of Patent: Feb. 23, 2016

(54) NONCONTACT CALIPER MEASUREMENTS OF SHEET PRODUCTS USING INTERSECTING LINES IN SHEET MANUFACTURING OR PROCESSING SYSTEMS

(75) Inventors: John F. Shakespeare, Hiltulanlahti (FI); Taria T. Shakespeare, Hiltulanlahti (FI)

(73) Assignee: Honeywell International Inc., Morris Plains, NJ (US)

( * ) Notice: Subject to any disclaimer, the term of this patent is extended or adjusted under 35 U.S.C. 154(b) by 680 days.

(21) Appl. No.: 13/492,404

(22) Filed: Jun. 8, 2012

(65) Prior Publication Data
US 2013/0329037 A1    Dec. 12, 2013

(51) Int. Cl.
*B65H 43/00*    (2006.01)
*G01B 11/06*    (2006.01)
*B65H 26/00*    (2006.01)
*G01N 21/86*    (2006.01)

(52) U.S. Cl.
CPC ............... *B65H 43/00* (2013.01); *B65H 26/00* (2013.01); *G01B 11/06* (2013.01); *B65H 2511/13* (2013.01); *B65H 2511/413* (2013.01); *B65H 2553/46* (2013.01); *B65H 2557/64* (2013.01); *B65H 2801/84* (2013.01); *G01N 2021/8663* (2013.01)

(58) Field of Classification Search
CPC ... G01N 21/88; G01N 21/89; G01N 21/8903; G01N 21/8806; H04N 7/18; H04N 7/183; H04N 7/188; G06T 7/0022; G06T 7/0004; G01B 11/002; G01B 11/005; G01B 11/02; G01B 11/026; G01B 11/028; G01B 11/06; G01B 11/0625; G01B 11/0691; G01B 11/26

USPC ......... 348/88, 86, 92, 134, 135, 136, 139, 41; 382/108, 111, 102
See application file for complete search history.

(56) References Cited

U.S. PATENT DOCUMENTS 4,040,748 A * 8/1977 Belleson et al. ............... 356/431
4,801,808 A * 1/1989 Hamasaki ...................... 250/548
5,637,849 A * 6/1997 Wang et al. .................... 235/454

(Continued)

FOREIGN PATENT DOCUMENTS

EP       1 321 903 A1    6/2003
WO    WO 03/002936 A1    1/2003

OTHER PUBLICATIONS

Pak Hui, "Laser Caliper Sensor Model 4213", Honeywell, Jun. 2005, 36 pages.

(Continued)

*Primary Examiner* — Mehrdad Dastouri
*Assistant Examiner* — Jimmy S Lee

(57) ABSTRACT

A method includes obtaining multiple images of a sheet of material. The images contain a first line projected onto a first side of the sheet and a second line projected onto a second side of the sheet. The images include (i) at least one first image containing the first line reflected off the first side of the sheet and the second line transmitted through the sheet and (ii) at least one second image containing the second line reflected off the second side of the sheet and the first line transmitted through the sheet. The method also includes identifying at least one point of intersection in the images where the lines intersect on the sheet. The method further includes identifying a caliper of the sheet using the at least one point of intersection.

20 Claims, 8 Drawing Sheets

(56) References Cited

U.S. PATENT DOCUMENTS

| | | | | |
|---|---|---|---|---|
| 6,038,028 | A | * | 3/2000 | Grann et al. .................. 356/630 |
| 6,281,679 | B1 | | 8/2001 | King et al. |
| 7,034,324 | B2 | * | 4/2006 | Voser ............................ 250/556 |
| 7,592,608 | B2 | | 9/2009 | Shakespeare et al. |
| 7,847,943 | B2 | | 12/2010 | Hellstrom et al. |
| 8,083,895 | B2 | | 12/2011 | Alev et al. |
| 2003/0011789 | A1 | * | 1/2003 | Shirley .......................... 356/630 |
| 2008/0063307 | A1 | * | 3/2008 | De Haan ....................... 382/300 |
| 2010/0020168 | A1 | | 1/2010 | Ye |

OTHER PUBLICATIONS

Frank M. Haran, et al., "System and Method for Correcting Caliper Measuremenmts of Sheet Products in Sheet Manufacturing or Processing Systems", U.S. Appl. No. 13/460,275, filed Apr. 30, 2012.

Notification of Transmittal of the International Search Report and the Written Opinion of the International Searching Authority, or the Declaration dated Aug. 21, 2013 in connection with International Patent Application No. PCT/US2013/040699.

Supplementary European Search Report dated Dec. 10, 2015 in connection with European Patent Application No. EP 13 80 1075.

* cited by examiner

NONCONTACT CALIPER MEASUREMENTS OF SHEET PRODUCTS USING INTERSECTING LINES IN SHEET MANUFACTURING OR PROCESSING SYSTEMS

TECHNICAL FIELD

This disclosure relates generally to measurement and control systems. More specifically, this disclosure relates to noncontact caliper measurements of sheet products using intersecting lines in sheet manufacturing or processing systems.

BACKGROUND

Webs or other sheets of material are used in a variety of industries and in a variety of ways. These materials can include paper, multi-layer paperboard, and other products manufactured or processed in long sheets. As a particular example, long sheets of paper can be manufactured and collected in reels. These sheets of material are often manufactured or processed at high rates of speed, such as speeds of up to one hundred kilometers per hour or more.

It is often necessary or desirable to measure one or more properties of a sheet of material as the sheet is being manufactured or processed. For example, it is often desirable to measure the caliper (thickness) of a paper sheet or other sheet being manufactured to verify whether the sheet's caliper is within certain specifications. Adjustments can then be made to the sheet-making process to ensure that the sheet's caliper stays within a desired range.

SUMMARY

This disclosure provides noncontact caliper measurements of sheet products using intersecting lines in sheet manufacturing or processing systems.

In a first embodiment, a method includes obtaining multiple images of a sheet of material. The images contain a first line projected onto a first side of the sheet and a second line projected onto a second side of the sheet. The images include (i) at least one first image containing the first line reflected off the first side of the sheet and the second line transmitted through the sheet and (ii) at least one second image containing the second line reflected off the second side of the sheet and the first line transmitted through the sheet. The method also includes identifying at least one point of intersection in the images where the lines intersect on the sheet. The method further includes identifying a caliper of the sheet using the at least one point of intersection.

In a second embodiment, a non-transitory computer readable medium embodies a computer program that includes computer readable program code for performing the method.

In a third embodiment, a system includes multiple illumination sources configured to project a first line onto a first side of a sheet and a second line onto a second side of the sheet. The system also includes multiple detectors configured to obtain multiple images of the sheet. The images include (i) at least one first image containing the first line reflected off the first side of the sheet and the second line transmitted through the sheet and (ii) at least one second image containing the second line reflected off the second side of the sheet and the first line transmitted through the sheet. The system further includes at least one processing device configured to identify at least one point of intersection in the images where the lines intersect on the sheet and identify a caliper of the sheet using the at least one point of intersection.

In a fourth embodiment, an apparatus includes at least one memory configured to store multiple images of a sheet of material. The images contain a first line projected onto a first side of the sheet and a second line projected onto a second side of the sheet. The images include (i) at least one first image containing the first line reflected off the first side of the sheet and the second line transmitted through the sheet and (ii) at least one second image containing the second line reflected off the second side of the sheet and the first line transmitted through the sheet. The apparatus also includes at least one processing device configured to identify at least one point of intersection in the images where the lines intersect on the sheet and identify a caliper of the sheet using the at least one point of intersection.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 7, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
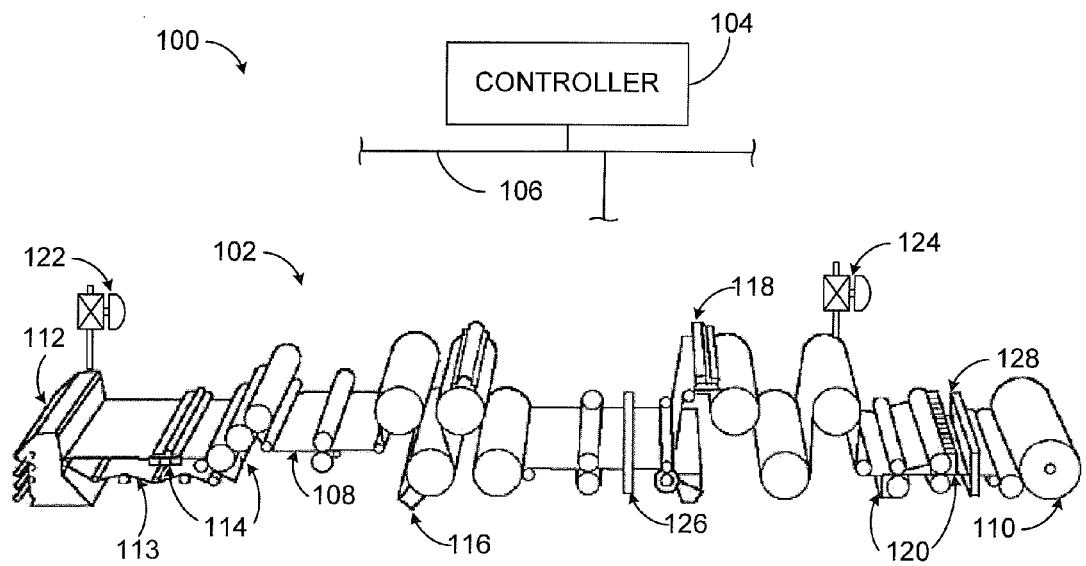
FIG. 1 illustrates an example sheet manufacturing or processing system according to this disclosure.

FIG. 1 illustrates an example sheet manufacturing or processing system 100 according to this disclosure. In this example, the system 100 includes a paper machine 102, a controller 104, and a network 106. The paper machine 102 includes various components used to produce a paper product, namely a paper sheet 108 that is collected at a reel 110. The controller 104 monitors and controls the operation of the paper machine 102, which may help to maintain or increase the quality of the paper sheet 108 produced by the paper machine 102.

In this example, the paper machine 102 includes at least one headbox 112, which distributes a pulp suspension uniformly across the machine onto a continuous moving wire screen or mesh 113. The pulp suspension entering the headbox 112 may contain, for example, 0.2-3% wood fibers, fillers, and/or other materials, with the remainder of the suspension being water. The headbox 112 may include an array of dilution actuators, which distributes dilution water into the pulp suspension across the sheet. The dilution water may be used to help ensure that the resulting paper sheet 108 has a more uniform basis weight across the sheet 108.

Arrays of drainage elements 114, such as vacuum boxes, remove as much water as possible to initiate the formation of the sheet 108. An array of steam actuators 116 produces hot steam that penetrates the paper sheet 108 and releases the latent heat of the steam into the paper sheet 108, thereby increasing the temperature of the paper sheet 108 in sections across the sheet. The increase in temperature may allow for easier removal of remaining water from the paper sheet 108. An array of rewet shower actuators 118 adds small droplets of water (which may be air atomized) onto the surface of the paper sheet 108. The array of rewet shower actuators 118 may be used to control the moisture profile of the paper sheet 108, reduce or prevent over-drying of the paper sheet 108, or correct any dry streaks in the paper sheet 108.

The paper sheet 108 is then often passed through a calender having several nips of counter-rotating rolls. Arrays of induction heating actuators 120 heat the shell surfaces of various ones of these rolls. As each roll surface locally heats up, the roll diameter is locally expanded and hence increases nip pressure, which in turn locally compresses the paper sheet 108. The arrays of induction heating actuators 120 may therefore be used to control the caliper (thickness) profile of the paper sheet 108. The nips of a calender may also be equipped with other actuator arrays, such as arrays of air showers or steam showers, which may be used to control the gloss profile or smoothness profile of the paper sheet.

Two additional actuators 122-124 are shown in FIG. 1. A thick stock flow actuator 122 controls the consistency of incoming stock received at the headbox 112. A steam flow actuator 124 controls the amount of heat transferred to the paper sheet 108 from drying cylinders. The actuators 122-124 could, for example, represent valves controlling the flow of stock and steam, respectively. These actuators may be used for controlling the dry weight and moisture of the paper sheet 108.

Additional components could be used to further process the paper sheet 108, such as a supercalender (for improving the paper sheet's thickness, smoothness, and gloss) or one or more coating stations (each applying a layer of coatant to a surface of the paper to improve the smoothness and printability of the paper sheet). Similarly, additional flow actuators may be used to control the proportions of different types of pulp and filler material in the thick stock and to control the amounts of various additives (such as retention aid or dyes) that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, this disclosure is not limited to use with systems for producing paper products and could be used with systems that process a paper product or with systems that produce or process other items or materials (such as multi-layer paperboard, cardboard, plastic, textiles, metal webs, or other or additional materials that are manufactured or processed as moving sheets).

In order to control the paper-making process, one or more properties of the paper sheet 108 may be continuously or repeatedly measured. The sheet properties can be measured at one or various stages in the manufacturing process. This information may then be used to adjust the paper machine 102, such as by adjusting various actuators within the paper machine 102. This may help to compensate for any variations of the sheet properties from desired targets, which may help to ensure the quality of the sheet 108.

As shown in FIG. 1, the paper machine 102 includes one or more scanners 126-128, each of which may include one or more sensors. Each scanner 126-128 is capable of measuring one or more characteristics of the paper sheet 108. For example, each scanner 126-128 could include sensors for measuring the caliper, anisotropy, basis weight, color, gloss, sheen, haze, surface features (such as roughness, topography, or orientation distributions of surface features), or any other or additional characteristics of the paper sheet 108.

Each scanner 126-128 includes any suitable structure or structures for measuring or detecting one or more characteristics of the paper sheet 108, such as one or more sets of sensors. The use of scanners represents one particular embodiment for measuring sheet properties. Other embodiments could be used, such as those including one or more stationary sets or arrays of sensors, deployed in one or a few locations across the sheet or deployed in a plurality of locations across the whole width of the sheet such that substantially the entire sheet width is measured.

The controller 104 receives measurement data from the scanners 126-128 and uses the data to control the paper machine 102. For example, the controller 104 may use the measurement data to adjust any of the actuators or other components of the paper machine 102. The controller 104 includes any suitable structure for controlling the operation of at least part of the paper machine 102, such as a computing device.

The network 106 is coupled to the controller 104 and various components of the paper machine 102 (such as the actuators and scanners). The network 106 facilitates communication between components of the system 100. The network 106 represents any suitable network or combination of networks facilitating communication between components in the system 100. The network 106 could, for example, represent a wired or wireless Ethernet network, an electrical signal network (such as a HART or FOUNDATION FIELDBUS network), a pneumatic control signal network, or any other or additional network(s).

Caliper measurements of the sheet 108 can be captured using one or more of the scanners 126-128. Conventional caliper sensors are often classified as full contact, semi-contact, or contactless. In a full contact caliper sensor, the sensor physically contacts both sides of a sheet. In a semi-contact caliper sensor, the sensor physically contacts one side of a sheet. In either case, material from the sheet can foul the sensor, creating a bias over time. These types of sensors also typically create undesirable marks on the sheet, increase the risk of sheet breaks, and cannot provide reliable measurements near the sheet's edges. Noncontact caliper sensors do not physically contact either side of the sheet. Instead, conventional noncontact caliper sensors typically project a spot onto each side of the sheet and perform triangulation to measure the sheet's caliper. However, these sensors typically require that the spots be aligned on both sides of the sheet, and they are highly vulnerable to misalignment between the spots. This can be particularly problematic if the sheet flutters or otherwise moves near the sensor.

In accordance with this disclosure, one or more of the scanners 126-128 includes at least one noncontact caliper sensor that projects illumination lines onto the sheet 108 and measures the sheet's caliper at the intersection of those lines. The use of intersecting lines avoids the problems associated with misalignment of spots. Moreover, the use of a noncontact sensor avoids problems such as bias caused by fouling, sheet marking, and sheet breakage. In addition, this technique can be implemented using commercially available cameras, lasers, and optics, which can help to reduce the cost associated with the sensor.

One or more caliper sensors can be deployed at one or several fixed locations across the width of the sheet 108, or a caliper sensor can traverse some or all of the width of the sheet 108. The sheet's caliper and its variation may be measured and expressed in any suitable manner, such as a function of time and/or position. The caliper measurements can be provided to the controller 104 and used to adjust operation of the system 100. Additional details and example implementations of a noncontact caliper sensor using intersecting lines are provided below.

Although FIG. 1 illustrates one example of a sheet manufacturing or processing system 100, various changes may be made to FIG. 1. For example, other systems could be used to produce other paper or non-paper products. Also, while shown as including a single paper machine 102 with various components and a single controller 104, the system 100 could include any number of paper machines or other machinery having any suitable structure, and the system 100 could include any number of controllers. In addition, FIG. 1 illustrates one operational environment in which caliper measurements using intersecting lines can be used. This functionality could be used in any other suitable system.

Figure 2A:
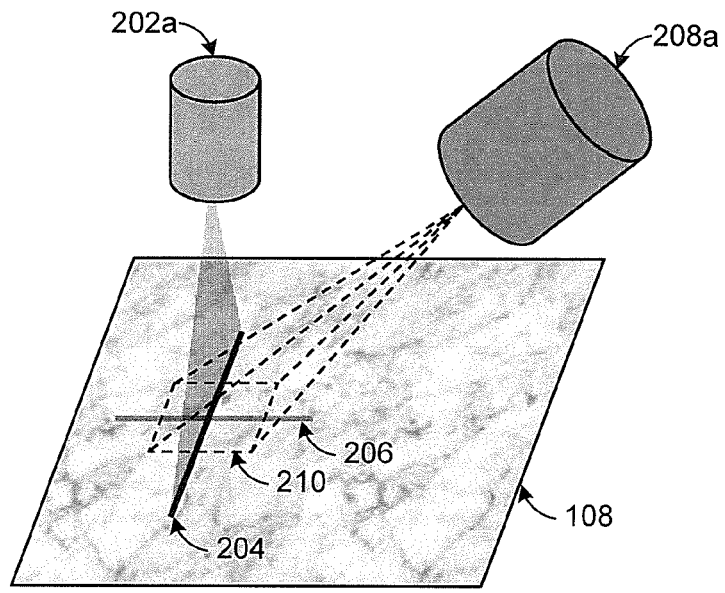
FIGS. 2A and 2B illustrate an example calculation of sheet caliper using intersecting lines according to this disclosure.
Figure 2B:
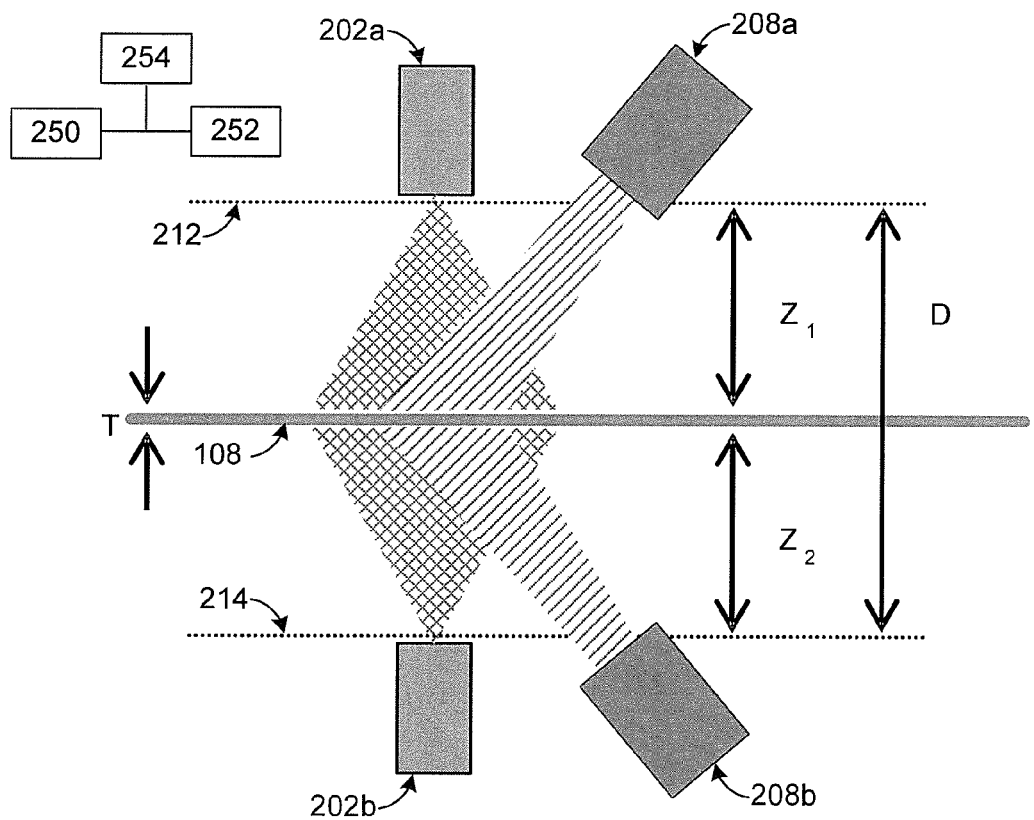

FIGS. 2A and 2B illustrate an example calculation of sheet caliper using intersecting lines according to this disclosure. As shown in FIG. 2A, a radiation source 202a in a caliper sensor projects an illumination line 204 onto one side of the sheet 108. Another radiation source 202b (shown in FIG. 2B) in the caliper sensor projects another illumination line 206 onto the opposite side of the sheet 108. The sheet 108 is not completely opaque to the radiation used, so the illumination line projected onto one side of the sheet 108 passes through the sheet 108 and can be detected on the opposite side of the sheet 108. As a result, each side of the sheet 108 has overlapping lines 204-206.

A detector 208a in the caliper sensor detects the radiation from the intersecting lines 204-206 within a specified area 210 on one side of the sheet 108. Another detector 208b (shown in FIG. 2B) in the caliper sensor detects the radiation from the intersecting lines 204-206 within the specified area 210 on the other side of the sheet 108. The detectors 208a-208b could capture this information in any suitable manner, such as by capturing visible or other images of the specified area 210.

As shown in FIG. 2B, the information captured by the detectors 208a-208b is analyzed, and various operations are performed to calculate the sheet caliper based on where the lines 204-206 interest. For example, a Z-sensor or other type of sensor could measure the total distance D between two planes 212-214. The caliper sensor could also identify the distance $Z_1$ between the plane 212 and the sheet 108 using triangulation calculations to the intersection of the lines 204-206. Further, the caliper sensor could identify the distance $Z_2$ between the plane 214 and the sheet 108 using triangulation calculations to the intersection of the lines 204-206. The caliper T of the sheet 108 can then be calculated by computing $D-Z_1-Z_2$.

The distance D may be measured using any suitable technique of adequate resolution in displacement and time. In this example, the distance D is measured between planes 212-214 in the caliper sensor. The planes 212-214 may be parallel to one another, and the planes 212-214 may be parallel to the nominal plane of the sheet 108. In other embodiments, the distance D is measured between points in the caliper sensor. The points may or may not be aligned, and if not aligned the distance D can be adjusted for the relative planar offset between those points. The planar offset could be measured in any suitable manner, such as a planar offset in two axes (which may be orthogonal and may coincide with machine and cross direction axes) or as a total planar offset in one axis.

In some embodiments, the illumination lines 204-206 represent thin lines, such as lines having a thickness of no more than about 0.5 mm. Each line 204-206 can extend lengthwise over any suitable distance, and the lines 204-206 may or may not have the same length. The lines 204-206 are at different angles in the plane of the sheet 108, and the triangulation to each surface of the sheet 108 is to the region where the lines 204-206 intersect. This can help to eliminate errors due to spot misalignment and sheet tilt.

Each radiation source 202a-202b includes any suitable structure for generating an illumination line, such as a laser or narrow-band light emitting diode (LED) and optics for focus and fine line generation. The radiation sources 202a-202b could generate radiation with substantially identical visible or other wavelengths, although different wavelengths can be used. For instance, near-infrared (NIR) wavelengths could be used for sheets 108 that are nearly opaque to visible wavelengths of light. Each detector 208a-208b includes any suitable structure for capturing information about lines projected onto a sheet, such as a charge-coupled device (CCD), a complimentary metal oxide semiconductor (CMOS) device, or a charge injection device (CID) and related optics. In addition to providing a focused image, the optics may include filters to exclude unwanted wavelengths of light from acquired images.

Note that the radiation sources 202a-202b could be pulsed or continuous devices, meaning the illumination lines 204-206 could be generated intermittently or continuously. If pulsing sources 202a-202b are used, the pulsing can be synchronized so that images are acquired either (i) with both lines 204-206 discernible in each image or (ii) with one line 204 visible in some images taken on both sides and with the other line 206 visible in other images taken on both sides. Pairs of images (one of the lines 204 and another of the lines 206) on each side can be taken in sufficiently quick succession, such as at the microsecond level, so that movement in the sheet position is negligible between the images. If continuous sources 202a-202b are used, the capture of images by the detectors 208a-208b can be synchronized so that the images are essentially captured simultaneously or are otherwise captured with a time difference sufficiently small so that the effect of movement of the sheet 108 does not significantly affect the caliper measurement.

Each line 204-206 can be projected normal to the nominal sheet surface or at any other suitable angle, such as in a plane at a right angle to the nominal specular plane of the sheet 108. The optical axis of each detector 208a-208b could be coplanar with the optical axis of the associated radiation source 202a-202b, but in a plane orthogonal to the plane in which the line is projected (such as 45° to that plane). The detectors 208a-208b could observe the lines 204-206 from azimuthal angles that are correspondingly at 90° to one another, although angles other than 90° could be used. Variations that deviate from these geometric arrangements are possible. For example, the optical axis of a detector could be normal to the nominal plane of the sheet 108, while a line projected onto the sheet 108 from that side could be projected at an angle to normal. Alternatively, both the optical axis of a detector and the line projected onto the sheet 108 from that side could be at angles to the normal. Such variations may involve additional steps in various calculations (such as using sine or cosine operations) and may have different sensitivities to errors in measurements.

The analysis of the images captured by the detectors 208a-208b could be performed by any suitable device or system. In some embodiments, the detectors 208a-208b are included within "smart" cameras, where some or all operations in the analysis of an image and the calculation of a triangulated distance to a point of intersection are done by each camera itself. In other embodiments, the detectors 208a-208b provide images or other information to an external device or system that processes the images and calculates the triangulated distances.

Figure 3A:
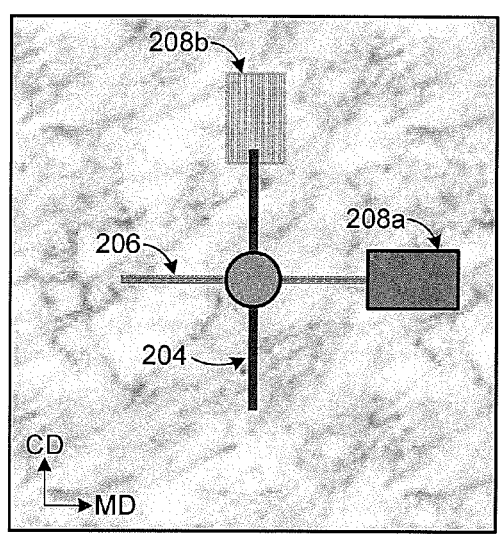
FIGS. 3A and 3B illustrate example projections of intersecting lines for caliper measurements according to this disclosure.
Figure 3B:
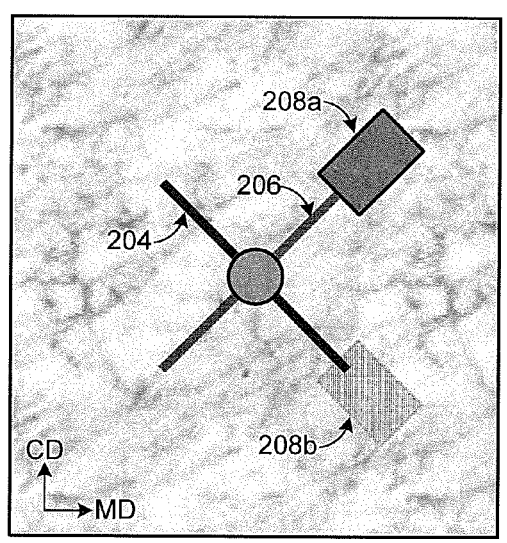

FIGS. 3A and 3B illustrate example projections of intersecting lines for caliper measurements according to this disclosure. In particular, FIGS. 3A and 3B illustrate example ways that the intersecting lines 204-206 can be projected onto the sheet 108.

In some embodiments, the lines 204-206 are projected at a relative angle of around 90° (meaning they are substantially perpendicular), although other angles could be used. In FIG. 3A, the line 204 is aligned with the cross direction (CD) of the sheet 108, while the line 206 is aligned with the machine direction (MD) of the sheet 108. The cross direction of the sheet 108 denotes the direction across the width of the sheet 108. The machine direction of the sheet 108 denotes the direction along the length of the sheet 108.

Since the scattering of light can differ between the MD and CD axes of fibrous mats such as paper, angles such as those shown in FIG. 3B could be used, where the lines 204-206 are at 45° angles with the cross and machine directions. The lines 204-206 can be projected in other directions with respect to the cross and/or machine direction.

The radiation forming the lines 204-206 could be unpolarized or have any suitable plane of polarization. The polarization of the sources 202a-202b can affect the dispersion of the lines 204-206 both in reflection off the sheet 108 and in transmission through the sheet 108. In some embodiments, each source 202a-202b has a polarization that is either (i) in the plane of the illumination line being formed or (ii) orthogonal to that plane. In other embodiments, both sources 202a-202b have a common plane of polarization, such as a plane that bisects either of the angles subtended by the illumination lines. If the illumination lines are at equal and opposite angles to the machine or cross direction, the plane of polarization could be in either the machine or cross direction axis. The plane of polarization could be controlled to avoid random polarization in the lines 204-206.

Figure 4A:
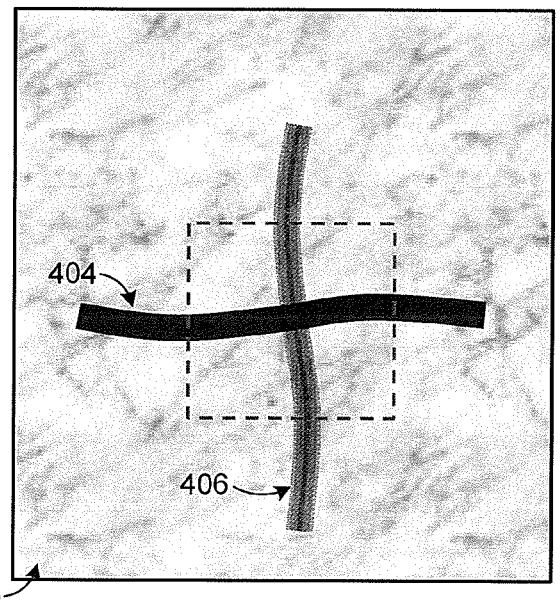
FIGS. 4A and 4B illustrate example compensation for nonlinear intersecting lines during caliper measurements according to this disclosure.
Figure 4B:
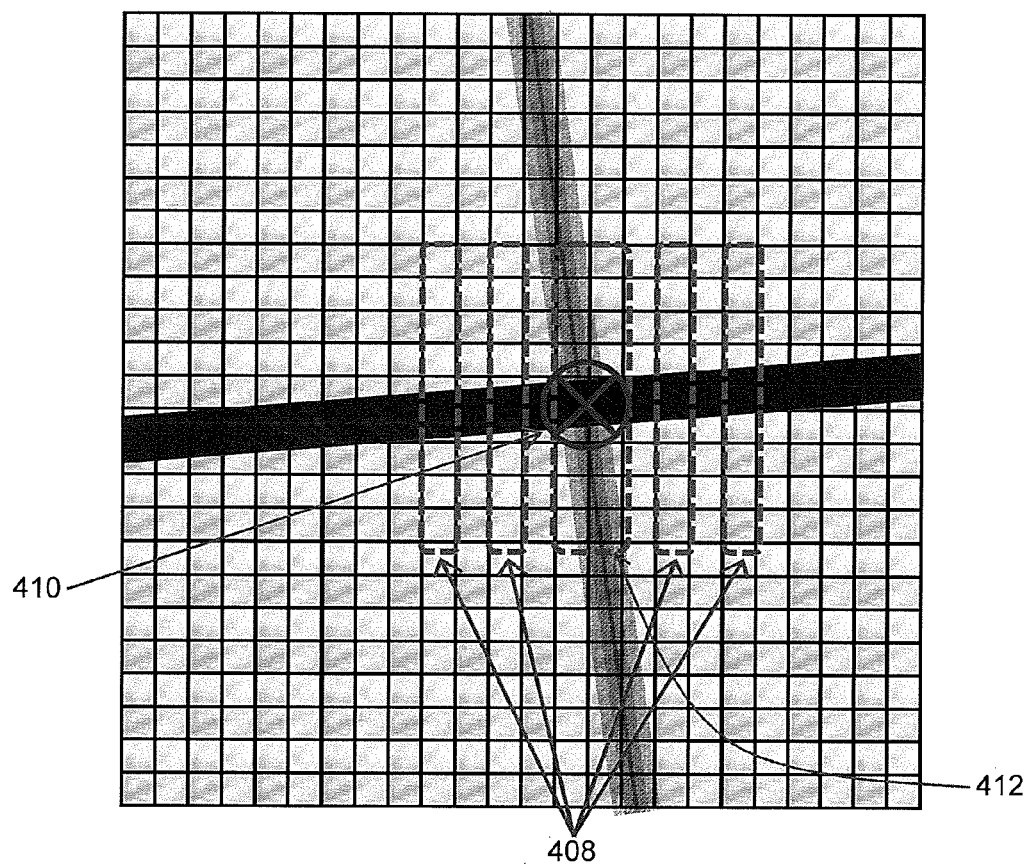

FIGS. 4A and 4B illustrate example compensation for non-linear intersecting lines during caliper measurements according to this disclosure. In FIGS. 2A, 3A, and 3B, the lines 204-206 are substantially straight when projected onto the sheet 108. However, the sheet 108 could tilt or otherwise move with respect to the radiation sources 202a-202b. Depending on how the sheet 108 moves, it is possible for the projected lines to become nonlinear. An example of this is shown in FIG. 4A, where lines 404-406 projected onto the sheet 108 are wavy. This could be due to tilt, fluttering, or other movement of the sheet 108.

To help compensate for this, an interpolating line or curve can be computed for at least one of the lines 404-406, and the interpolated line(s) can be used to more specifically identify the point of intersection. An example of this is shown in FIG. 4B, where one or more pixel groups 408 on each side of the point of intersection 410 are analyzed. An interpolated line can be generated based on the pixels in these pixel groups 408, and the interpolated line (rather than the actual line) is used to identify the point of intersection 410. Note that this could be done for one or both lines 404-406. Also note that a pixel group 412 that includes the actual point of intersection 410 may or may not be included in the interpolation.

Each pixel group 408 could include any suitable collection of pixels, such as pixels in a single row or column. The rows or columns may or may not be adjacent. In particular embodiments, within each pixel group 408, the local centroid of the line is identified, and the location of the line is identified with sub-pixel accuracy. The interpolation could be performed only for the transmitted line or for both the transmitted line and the reflected line. The transmitted line represents the line projected onto the opposing side of the sheet 108 from the detector and transmitted through the sheet 108. The reflected line represents the line projected onto the same side of the sheet 108 as the detector and reflected off the sheet 108. Any suitable interpolation could be used, such as linear interpolation or a function-based interpolation (like a cubic spline). Optionally, a least-squares approach could be used to fit each function to a larger number of points.

The process shown in FIG. 4B is not limited to use with wavy lines. For example, in some instances, the area where two illumination lines intersect can have bleedthrough where the lines lose clear boundaries. Interpolation could also be used here, where the lines in areas around the point of intersection are interpolated, and the interpolated lines are used to identify the point of intersection. If bleedthrough is not expected to be problematic, the point of intersection can be included in an interpolated line, or a simple triangulation to the point of intersection can be used directly.

It is also possible that a line generated by a radiation source 202a-202b is not uniform across its entire width. An example of this can be seen in FIGS. 4A and 4B, where the line 406 is more intense in its central area. Note that each line 404-406 need not be symmetric, meaning the area of greatest intensity need not be in the exact middle of the line. Non-uniformity of an illumination line can be detected in any suitable manner, such as by illuminating a smooth surface (like on a calibration target). An image of the illumination line can then be captured and analyzed to identify the portion of the line with the greatest intensity. This information could then be stored and used later. For instance, when identifying the point of intersection of two lines 204-206 or 404-406, the point of intersection can be identified as the area where the lines' greatest intensities meet. This may allow for more accurate caliper measurements or for the use of less precise illumination line generators.

In some embodiments, the calculation of the caliper of the sheet 108 can be done using at least one processing unit 250, such as a microprocessor, microcontroller, digital signal processor, application specific integrated circuit, field programmable gate array, or other computing or processing device. At least one memory 252 can store instructions and data used, generated, or collected by the processing unit(s) 250. At least one network interface 254 can be used to communicate with external devices or systems, such as to transmit caliper measurements to the controller 104 or other destination(s). In particular embodiments, the detectors 208a-208b include "smart" cameras, and each camera could include the components 250-254 to analyze the images obtained by that camera.

In other embodiments, the detectors 208a-208b provide captured images to the components 250-254, which analyze the images.

Figure 5A:
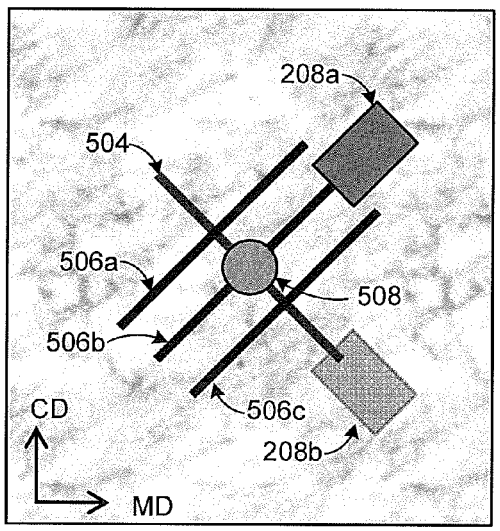
FIGS. 5A through 5C illustrate additional example projections of intersecting lines for caliper measurements according to this disclosure.
Figure 5B:
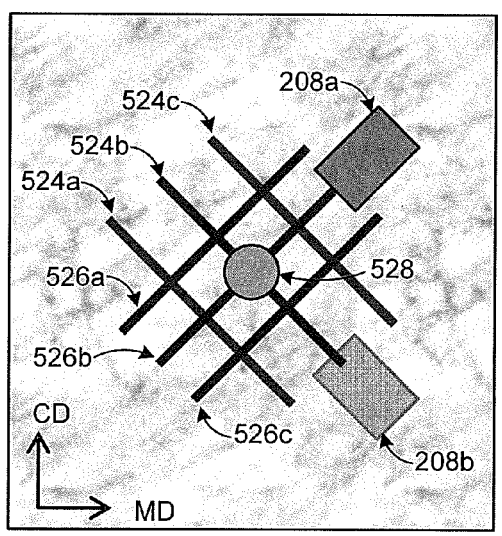
Figure 5C:
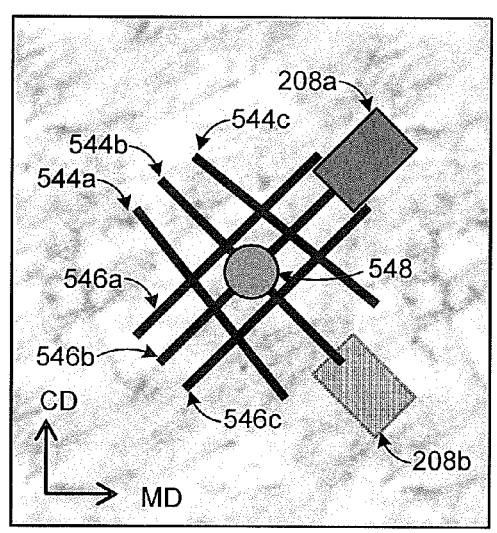

FIGS. 5A through 5C illustrate additional example projections of intersecting lines for caliper measurements according to this disclosure. While FIGS. 2A through 4B depict a single line projected onto the sheet 108 on each side, more than one line can be projected onto the sheet 108 from either or both sides.

In FIG. 5A, a single line 504 is projected onto the sheet 108 from one side, while three lines 506a-506c are projected onto the sheet 108 from the other side. The caliper of the sheet 108 may be measured using triangulation to one or more of the three points of intersection. Here, a single point of intersection 508 between the lines 504 and 506b is used. However, any other single point of intersection or combination of points of intersection could be used.

In FIG. 5B, three lines 524a-524c are projected onto the sheet 108 from one side, while three lines 526a-526c are projected onto the sheet 108 from the other side. The caliper of the sheet 108 may be measured using triangulation to one or more of the nine points of intersection. Here, a single point of intersection 528 between the lines 524b and 526b is used. However, any other single point of intersection or combination of points of intersection could be used.

When multiple lines are projected onto the sheet 108 on one side, they can be nominally parallel as shown in FIGS. 5A and 5B, although in either approach the lines could also be non-parallel. In FIG. 5C, three lines 544a-544c are projected onto the sheet 108 from one side, while three lines 546a-546c are projected onto the sheet 108 from the other side. On each side of the sheet 108, the lines are not parallel. However, the lines on each side of the sheet 108 are projected onto the sheet 108 so that they do not intersect in a region where those lines are expected to intersect with at least one line projected onto the opposite side of the sheet 108 (where that intersection is used for caliper measurement of the sheet). Again, the caliper of the sheet 108 may be measured using triangulation to one or more of the nine points of intersection. Here, a single point of intersection 548 between the lines 544b and 546b is used. However, any other single point of intersection or combination of points of intersection could be used.

When multiple lines are projected onto a single side of the sheet 108, the lines can be generated by one or multiple sources. When a single source is used, appropriate optics can be provided for generating multiple illumination lines from the single source. As noted above, when one or more pulsed sources are used, the lines need not be projected simultaneously on both sides of the sheet 108. Also note that the intersection(s) used in caliper measurements may include all intersections, a fixed subset of intersections, or a random subset of intersections. A subset of the intersections may be static or chosen dynamically for each pair of images. For example, the chosen intersections may be limited to those for which there are no saturated pixels in the images of the reflected lines, limited to those for which the intensity of the transmitted lines is highest, or limited to those for which a correspondence is clear between images acquired by the two detectors 208a-208b.

If the caliper of the sheet 108 is measured at multiple intersections, a final estimate of the caliper can be formed by combining multiple caliper measurements. For example, a final estimate may use the average of the measured caliper values. Similarly, uncertainty in the final caliper estimate or local variability in caliper measurements can be formed from the statistical distribution of the measured caliper values. As a particular example, the 95% confidence bounds of the caliper estimate may be represented by twice the statistical dispersion of the caliper measurements.

Although FIGS. 2A through 5C illustrate examples of the calculation of sheet caliper, the projections of intersecting lines, and the compensation for nonlinear intersecting lines, various changes may be made to FIGS. 2A through 5C. For example, as noted above, various geometries can be used with the sources 202a-202b and the detectors 208a-208b and with the illumination lines. Also, other mechanisms could be used to compensate for nonlinear intersecting lines. In addition, note that a combination of approaches described above could be used, such as when interpolation is used with multiple lines projected onto a single side of the sheet 108.

FIGS. 6A through 6D illustrate an example implementation of a caliper sensor 600 in a sheet manufacturing or processing system according to this disclosure. The caliper sensor 600 could, for example, be used in one or more of the scanners 126-128 shown in FIG. 1.

Figure 6A:
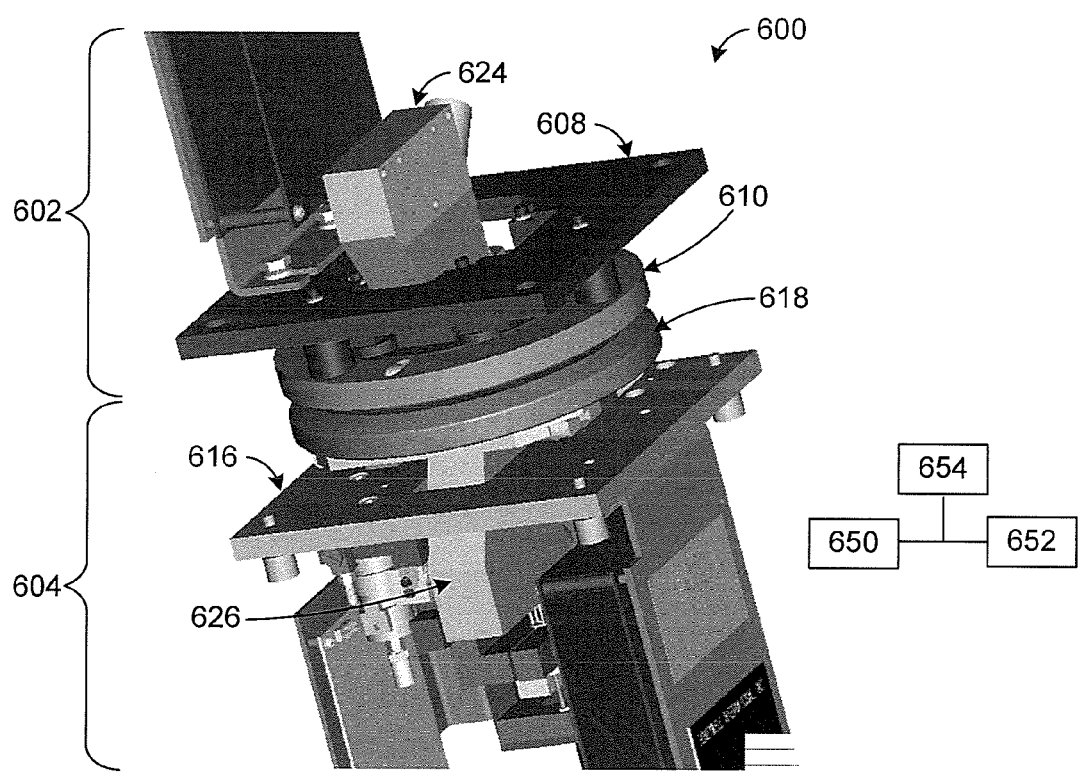
FIGS. 6A through 6D illustrate an example implementation of a caliper sensor in a sheet manufacturing or processing system according to this disclosure.
Figure 6B:
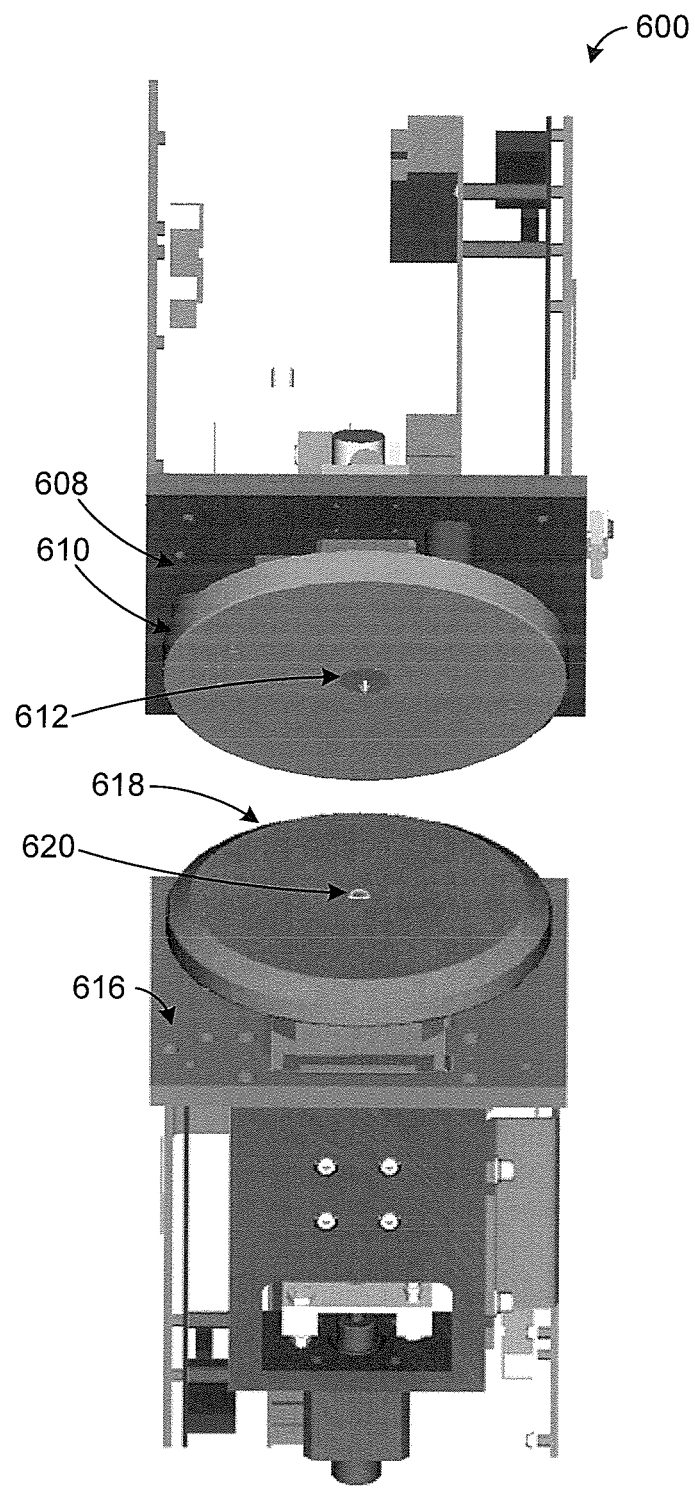

As shown in FIG. 6A, the caliper sensor 600 includes an upper sensor module 602 and a lower sensor module 604. The upper sensor module 602 in this example includes an upper sensor baseplate 608, which can be used to physically couple the upper sensor module 602 to another structure (such as a sensor platform that moves the upper sensor module 602 across a surface of the sheet 108). Other components of the upper sensor module 602 can be mounted or otherwise coupled to the upper sensor module 602. A sensor dust cover 610 denotes a structure that is placed near the sheet 108. The sensor dust cover 610 includes an aperture 612 as shown in FIG. 6B. The aperture 612 allows radiation to pass through the dust cover 610, both from a radiation source for delivery to the sheet 108 and to a detector after interaction with the sheet 108.

The lower sensor module 604 includes a lower sensor baseplate 616 and a lower sensor dust cover 618. The lower sensor baseplate 616 can be used to physically couple the lower sensor module 604 to another structure (such as a sensor platform that moves the lower sensor module 604 across another surface of the sheet 108). Other components of the lower sensor module 604 can be mounted or otherwise coupled to the lower sensor module 604. The lower sensor dust cover 618 serves various functions, such as providing a target for an eddy current sensor (a Z-sensor 627 as described below). The sheet 108 passes through a gap between the upper and lower sensor modules 602-604. The lower sensor dust cover 618 includes an aperture 620 as shown in FIG. 6B.

Each sensor module 602-604 includes any suitable structure for placement near a sheet and for facilitating caliper measurements of the sheet. Each sensor baseplate 608, 616 includes any suitable structure for physically coupling a sensor module to an external structure (such as a sensor platform). Each aperture 612, 620 represents any suitable opening or other mechanism allowing passage of radiation.

In this example, a distance measurement unit 624 is mounted to the upper sensor baseplate 608 via another component (the Z-sensor 627), and a distance measurement unit 626 is mounted to the lower sensor baseplate 616. The distance measurement units 624-626 perform non-contact distance measuring operations to measure distance to opposing sides of the sheet 108. For example, each distance measurement unit 624-626 could generate illumination lines that are projected onto the sheet 108, where the lines intersect one another. Each distance measurement unit 624-626 could also capture images of the intersecting lines and possibly perform triangulation operations to measure distance to each side of the sheet 108. Alternatively, each distance measurement unit 624-626 could provide its images or other data to an external component that performs triangulation operations.

Each distance measurement unit 624-626 includes any suitable structure for optically projecting one of multiple intersecting lines and capturing information about the intersecting lines. For instance, each distance measurement unit 624-626 could include one of the sources 202a-202b and one of the detectors 208a-208b.

Figure 6C:
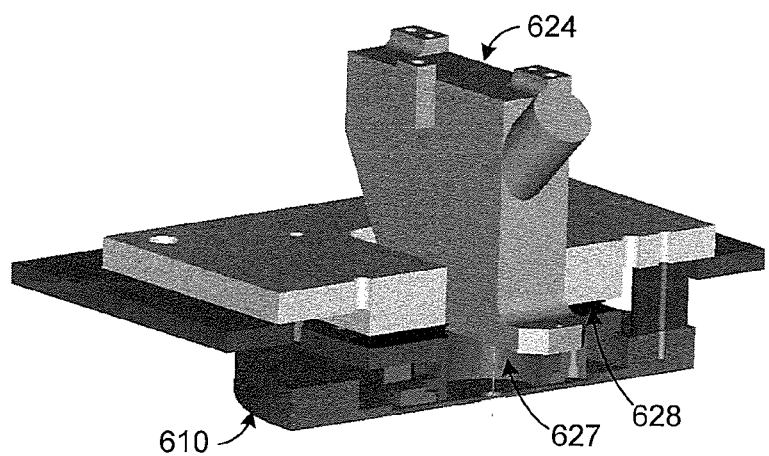

FIG. 6C illustrates additional details of portions of the upper sensor module 602. As shown here, the distance measurement unit 624 is mounted to the Z-sensor 627, which in turn is mounted to the upper sensor baseplate 608. The upper sensor module 602 also includes a cooler 628. The Z-sensor 627 includes a sensing coil for an eddy current sensor or an inductive proximity sensor and measures the distance to the lower sensor dust cover 618. As described above, this distance can be used as the distance D to determine the caliper of the sheet 108. The Z-sensor 627 includes any suitable structure for wirelessly measuring distance, such as an inductive sensor coil that generates eddy current in the sensor dust cover 618. The cooler 628 helps to maintain the temperature of the Z-sensor 627. The cooler 628 includes any suitable structure for cooling a structure, such as a Peltier cooler.

Figure 6D:
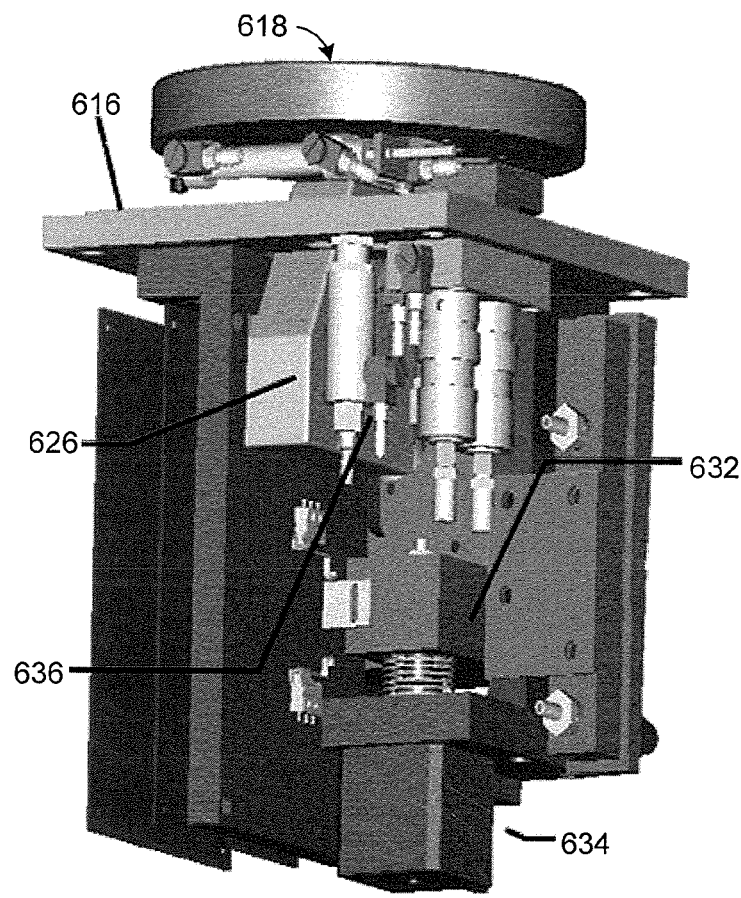

FIG. 6D illustrates additional details of portions of the lower sensor module 604. As shown here, the distance measurement unit 626 is mounted on the lower sensor baseplate 616. The lower sensor module 604 also includes a movable stage that can move the sensor dust cover 618. Movement of the sensor dust cover 618 can be done during calibration and other operations involving the Z-sensor 627. In particular, the Z-sensor 627 creates eddy currents in the sensor dust cover 618, and precise positioning of the sensor dust cover 618 can be performed using the movable stage.

In this example, a precision slide 632 moves the sensor dust cover 618 and is actuated by a stepper motor 634. A sensor 636 measures the movement of the sensor dust cover 618, such as with sub-micron precision. The sensor dust cover 618 includes any suitable conductive structure supporting operation of a Z-sensor. The precision slide 632 includes any suitable structure for moving an eddy current sensor's target. The motor 634 includes any suitable structure for moving a precision slide to thereby move an eddy current sensor's target. The sensor 636 includes any suitable structure for measuring a position of an eddy current sensor's target, such as a linear variable differential transformer or a high precision optical encoder.

In some embodiments, the caliper sensor 600 includes at least one processing unit 650, at least one memory 652, and at least one network interface 654. The at least one processing unit 650 can be responsible for processing the images captured by the caliper sensor 600. In particular embodiments, the upper and lower sensor modules 602-604 include "smart" cameras, and each camera could include the components 650-654 to analyze the images obtained by that camera. In other embodiments, the upper and lower sensor modules 602-604 provide captured images to the components 650-654, which reside outside the modules 602-604.

Although FIGS. 6A through 6D illustrate one example of a caliper sensor 600 in a sheet manufacturing or processing system, various changes may be made to FIGS. 6A through 6D. For example, each component shown in these figures could have any suitable size, shape, and dimensions and can be formed from any suitable material(s). Also, one or more components shown in these figures could be omitted if the functions associated with those components are not needed. For instance, while a Z-sensor 627 and a movable target (dust cover 618) represent one possible way to measure the distance D, other approaches could also be used. In addition, the use of intersecting lines for caliper measurements can be done with any other suitable caliper sensor and is not limited to use with just the caliper sensor 600 shown here.

Figure 7:
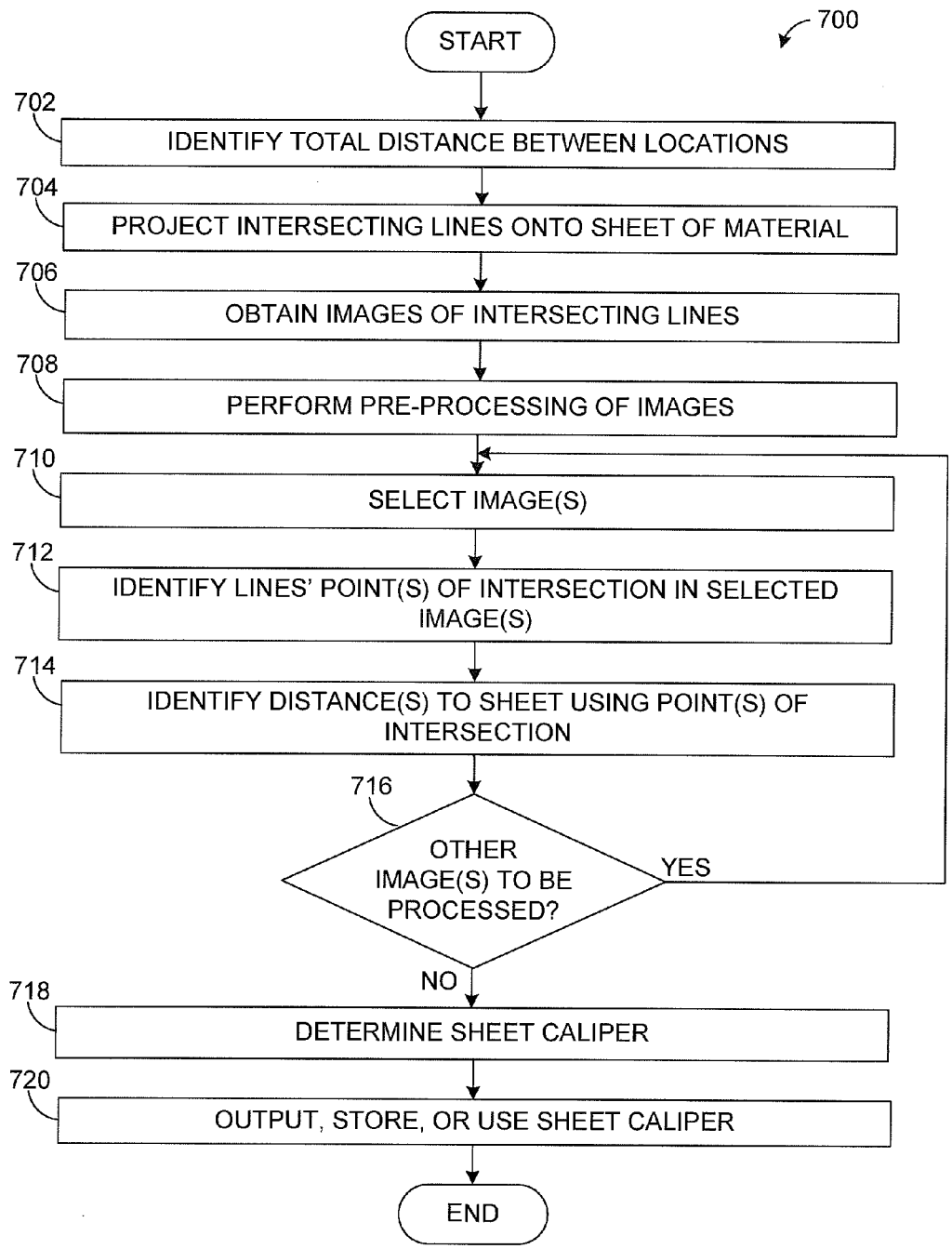
FIG. 7 illustrates an example method for caliper measurement using intersecting lines in a sheet manufacturing or processing system according to this disclosure.

FIG. 7 illustrates an example method 700 for caliper measurement using intersecting lines in a sheet manufacturing or processing system according to this disclosure. For ease of explanation, the method 700 is described with respect to a caliper sensor containing the components shown in FIGS. 2A and 2B. The method 700 could be used by any other suitable caliper sensor, such as the sensor 600.

As shown in FIG. 7, a total distance between two locations is identified at step 702. This could include, for example, the caliper sensor using a Z-sensor or other mechanism to identify a distance between two planes 212-214 or two points within the caliper sensor. This could occur once or any number of times.

Intersecting lines are projected onto a sheet of material at step 704. This could include, for example, the radiation sources 202a-202b projecting illumination lines 204-206 onto the sheet 108. The illumination lines 204-206 could include visible or other radiation at any suitable wavelength(s). As noted above, the lines 204-206 could be projected simultaneously onto the sheet 108 or individually in rapid succession. Moreover, one or multiple lines could be projected onto each side of the sheet 108, and the lines may or may not be parallel.

Images of the intersecting lines are obtained at step 706. This could include, for example, the detectors 208a-208b capturing images of the lines 204-206 on the sheet 108. If the lines 204-206 are projected at the same time, each image could include both lines 204-206. If the lines 204-206 are projected serially, each image could include one of the lines 204-206, and pairs of images can be used. The images can be preprocessed at step 708. This could include, for example, the caliper sensor correcting the images for geometric distortions caused by lens characteristics.

At least one of the images is selected at step 710. This could include, for example, the caliper sensor selecting one image containing both lines 204-206 or a pair of images each containing one of the lines 204-206.

The lines' point or points of intersection are identified in the selected image(s) at step 712. This could include, for example, the caliper sensor directly identifying the point where the two lines 204-206 meet. This could also include the caliper sensor interpolating one or more of the lines 204-206 around the point of intersection (and possibly including the point of intersection) and using the interpolated line(s) to identify the point of intersection. This could further include the caliper sensor identifying the point of intersection while considering nonlinear intensities across the width(s) of the line(s) 204-206. If multiple lines are projected onto one side of the sheet 108, this may also include the caliper sensor identifying a particular point of intersection or multiple points of intersection.

At least one distance to the sheet is identified using the point(s) of intersection at step 714. This could include, for example, the caliper sensor performing triangulation calculations to identify the distance from a known location (such as a plane 212-214 or other plane) to each point of intersection. If multiple points of intersection have been identified, this could include identifying the distance to one point of intersection or multiple points of intersection.

In some embodiments, the lines' point(s) of intersection and the distance to the sheet 108 are calculated differently depending on the relative intensities of the transmitted and reflected lines 204-206. The relative intensities of the lines 204-206 can be established in any suitable manner. For example, the relative intensities could be determined using selected pixel groups around the lines' actual or approximated point of intersection. As a particular example, a weighted or unweighted average, the maximum of each pixel group, or a percentage of each pixel group can be used to calculate the lines' intensities.

If the intensity of the transmitted line is much less than the intensity of the reflected line, the direct identification of a point of intersection may be performed. Here, coordinates $X_i$ and $Y_i$ for the point of intersection can be estimated, such as by using the local centroid of the lines' intensities. This could give a result with sub-pixel resolution, which could be converted into units of distance (such as μm).

If the intensity of the transmitted line is not sufficiently less than the intensity of the reflected line, various approaches could be used. For example, a number of locations $X_k$ can be chosen in the reflected line on either side of the point of intersection, and the $Y_k$ location of the reflected line is estimated at each $X_k$ location. The $X_k$ locations could correspond to single rows/columns of pixels (which may or may not be adjacent) or to contiguous groups of rows/columns. Estimation of the $Y_k$ location could use the local centroid of the reflected line intensity at each $X_k$ location, and each $Y_k$ result could have sub-pixel accuracy. The $Y_i$ location of the point of intersection can be interpolated from the line or curve formed by the $(X_k, Y_k)$ pairs for a previously estimated $X_i$ value. The interpolation could use a function-based interpolation (such as a cubic spline) between similar numbers of $(X_k, Y_k)$ points on either side of $X_i$, optionally using least-squares to fit the function to a larger number of points. The interpolation could also use a linear interpolation between the $(X_k, Y_k)$ points on either side of $X_i$.

In either case, the distance to a point of intersection could then be estimated using triangulation based on known geometries, such as the relative positions of the planes 212-214 and the imaging axis. For example, if the plane of illumination is normal to the nominal sheet plane and the detector axis is at angle $\Theta$ to normal in elevation and 90° in azimuth relative to the illumination plane, the distance $Z_i$ to the surface of the sheet 108 at the point of intersection could be calculated as:

$$Z_i = Z_0 + Y_i \operatorname{cosec} \Theta$$

where $Z_0$ is a known distance offset to the edge of the image in the illumination plane. Ideally, the image(s) being processed are undistorted or have been preprocessed to remove distortion. If not, a correction may be needed to $Y_i$ before the triangulation is performed. The correction can be based on both the $X_i$ and $Y_i$ locations in the distorted image. Alternatively, correction for distortion may be incorporated directly into the triangulation calculations.

In other embodiments, the distance to the point of intersection could be determined as follows. The distance to each $X_k$ location can be estimated using triangulation based on known geometries, such as the relative positions of the planes 212-214 and the imaging axis. For example, if the illumination plane is normal to the nominal sheet plane and the detector axis is at angle $\Theta$ to normal in elevation and 90° in azimuth relative to the illumination plane, the distance $Z_k$ to the surface of the sheet 108 based on the location $Y_k$ estimated for $X_k$ could be calculated as:

$$Z_k = Z_0 + Y_k \operatorname{cosec} \Theta$$

Again, the analyzed image(s) could be undistorted, or a correction may be done before, during, or after the triangulation is performed. The final distance to the sheet 108 at the actual point of intersection can be estimated by interpolating on the line or curve formed by the pairs $(X_k, Z_k)$ to find the value of $Z_i$ that corresponds to the estimated $X_i$. Again, the interpolation could use a function-based interpolation (like a cubic spline) between similar numbers of $(X_k, Z_k)$ points on either side of $X_i$ (optionally using least-squares) or a linear interpolation between the $(X_k, Z_k)$ points on either side of $X_i$.

A determination is made whether more images remain to be processed at step 716. If so, the method 700 returns to step 710 to select one or more additional images. This may allow, for example, the distance to each side of the sheet 108 to be determined. Note that the distance to both sides of the sheet 108 could be determined using images obtained substantially simultaneously, although this is not required. Some delay between images could be acceptable as long as the sheet 108 does not move out of its current plane (as changes in the sheet's planar position would affect the caliper measurement).

The sheet caliper is determined at step 718. This could include, for example, the caliper sensor determining the caliper based on the total distance determined in step 702 and the individual distances determined in step 714. As a particular example, the caliper or thickness T of the sheet 108 can be given as:

$$T \times D - (Z_1 + Z_2)$$

where $Z_1$ represents a measured distance from a first surface of the sheet 108 to a reference plane (such as plane 212), $Z_2$ represents a measured distance from a second surface of the sheet 108 to a reference plane (such as plane 214), and D represents a known distance between the reference planes. Various constants may be included in this calculation to take into account the construction of the caliper sensor, such as offset distances between the planes 212-214 and the planes from which $Z_1$ and $Z_2$ are measured.

The caliper measurement is output, stored, or used in some manner at step 720. This could include, for example, the caliper sensor outputting the caliper measurement to the controller 104 for use in adjusting the sheet manufacturing or processing system. This could also include the caliper sensor providing the caliper measurement to a historian or other database for short-term or long-term storage. The caliper measurement could be used in any other suitable manner.

Although FIG. 7 illustrates one example of a method 700 for caliper measurement using intersecting lines in a sheet manufacturing or processing system, various changes may be made to FIG. 7. For example, while shown as a series of steps, various steps in FIG. 7 could overlap, occur in parallel, occur in a different order, or occur multiple times. As a particular example, the images from different detectors could be analyzed in parallel.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "transmit" and "receive," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. Various values are given above, such as angles or distances. These values are approximate values only.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
    obtaining multiple images of a sheet of material, the images containing a first line projected onto a first side of the sheet and a second line projected onto a second side of the sheet, the images comprising:
        at least one first image of the first side of the sheet, the at least one first image containing the first line reflected off the first side of the sheet and the second line transmitted through the sheet to the first side of the sheet; and
        at least one second image of the second side of the sheet, the at least one second image containing the second line reflected off the second side of the sheet and the first line transmitted through the sheet to the second side of the sheet;
    identifying at least one point of intersection in the images where the lines intersect on the sheet; and
    identifying a caliper of the sheet using the at least one point of intersection.

2. The method of claim 1, wherein identifying the at least one point of intersection comprises:
    identifying a first point of intersection in the at least one first image; and
    identifying a second point of intersection in the at least one second image.

3. The method of claim 2, wherein identifying the caliper of the sheet comprises:
    identifying a first distance to the first side of the sheet using the first point of intersection;
    identifying a second distance to the second side of the sheet using the second point of intersection; and
    identifying the caliper of the sheet using the first and second distances.

4. The method of claim 1, wherein:
    multiple lines are projected onto each of at least one side of the sheet; and
    identifying the at least one point of intersection comprises identifying multiple points of intersection.

5. The method of claim 4, wherein:
    identifying the caliper of the sheet comprises identifying multiple caliper measurements, the multiple caliper measurements identified using multiple distances to each of at least one side of the sheet based on the multiple points of intersection; and
    identifying a final caliper measurement using the multiple caliper measurements.

6. The method of claim 1, wherein identifying the at least one point of intersection comprises:
    identifying multiple points associated with one of the lines in multiple pixel groups, including pixel groups around an estimated point of intersection;
    generating an interpolated line or curve using the multiple points; and
    identifying an actual point of intersection using the interpolated line.

7. The method of claim 6, wherein the multiple pixel groups comprise a pixel group containing the estimated point of intersection.

8. The method of claim 1, wherein:
    at least one of the lines has a non-uniform intensity across its width;
    the method further comprises identifying a portion of at least one of the lines having a maximum intensity; and
    identifying the at least one point of intersection comprises identifying a point of intersection using the identified portion of at least one of the lines.

9. The method of claim 1, wherein the first and second lines are at an angle of about 45° with respect to a cross direction across a width of the sheet and an angle of about 45° with respect to a machine direction along a length of the sheet.

10. A system comprising:
    multiple illumination sources configured to project a first line onto a first side of a sheet and a second line onto a second side of the sheet;
    multiple detectors configured to obtain multiple images of the sheet, the images comprising:
        at least one first image of the first side of the sheet, the at least one first image containing the first line reflected off the first side of the sheet and the second line transmitted through the sheet to the first side of the sheet; and
        at least one second image of the second side of the sheet, the at least one second image containing the second line reflected off the second side of the sheet and the first line transmitted through the sheet to the second side of the sheet; and
    at least one processing device configured to identify at least one point of intersection in the images where the lines intersect on the sheet and identify a caliper of the sheet using the at least one point of intersection.

11. The system of claim 10, wherein the at least one processing device is configured to:
    identify a first point of intersection in the at least one first image; and
    identify a second point of intersection in the at least one second image.

12. The system of claim 11, wherein the at least one processing device is configured to:
- identify a first distance to the first side of the sheet using the first point of intersection;
- identify a second distance to the second side of the sheet using the second point of intersection; and
- identify the caliper of the sheet using the first and second distances.

13. The system of claim 10, wherein:
- the illumination sources are configured to project multiple lines onto each of at least one side of the sheet; and
- the at least one processing device is configured to identify multiple points of intersection.

14. The system of claim 13, wherein the at least one processing device is configured to:
- identify multiple caliper measurements using multiple distances to each of at least one side of the sheet based on the multiple points of intersection; and
- identify a final caliper measurement using the multiple caliper measurements.

15. The system of claim 10, wherein the at least one processing device is configured to:
- identify multiple points associated with one of the lines in multiple pixel groups in at least one of the images, the multiple pixel groups including pixel groups around an estimated point of intersection;
- generate an interpolated line or curve using the multiple points; and
- identify an actual point of intersection using the interpolated line.

16. An apparatus comprising:
- at least one memory configured to store multiple images of a sheet of material, the images containing a first line projected onto a first side of the sheet and a second line projected onto a second side of the sheet, the images comprising:
  - at least one first image of the first side of the sheet, the at least one first image containing the first line reflected off the first side of the sheet and the second line transmitted through the sheet to the first side of the sheet; and
  - at least one second image of the second side of the sheet, the at least one second image containing the second line reflected off the second side of the sheet and the first line transmitted through the sheet to the second side of the sheet; and
- at least one processing device configured to identify at least one point of intersection in the images where the lines intersect on the sheet and identify a caliper of the sheet using the at least one point of intersection.

17. The apparatus of claim 16, wherein the at least one processing device is configured to:
- identify a first point of intersection in the at least one first image;
- identify a second point of intersection in the at least one second image;
- identify a first distance to the first side of the sheet using the first point of intersection;
- identify a second distance to the second side of the sheet using the second point of intersection; and
- identify the caliper of the sheet using the first and second distances.

18. The apparatus of claim 16, wherein:
- the images contain multiple lines projected onto each of at least one side of the sheet; and
- the at least one processing device is configured to:
  - identify multiple points of intersection;
  - identify multiple caliper measurements using multiple distances to each of at least one side of the sheet based on the multiple points of intersection; and
  - identify a final caliper measurement using the multiple caliper measurements.

19. The apparatus of claim 16, wherein the at least one processing device is configured to:
- identify multiple points associated with one of the lines in multiple pixel groups in at least one of the images, the multiple pixel groups including pixel groups around an estimated point of intersection;
- generate an interpolated line or curve using the multiple points; and
- identify an actual point of intersection using the interpolated line.

20. A non-transitory computer readable medium embodying a computer program, the computer program comprising computer readable program code for:
- obtaining multiple images of a sheet of material, the images containing a first line projected onto a first side of the sheet and a second line projected onto a second side of the sheet, the images comprising:
  - at least one first image of the first side of the sheet, the at least one first image containing the first line reflected off the first side of the sheet and the second line transmitted through the sheet to the first side of the sheet; and
  - at least one second image of the second side of the sheet, the at least one second image containing the second line reflected off the second side of the sheet and the first line transmitted through the sheet to the second side of the sheet;
- identifying at least one point of intersection in the images where the lines intersect on the sheet; and
- identifying a caliper of the sheet using the at least one point of intersection.

\* \* \* \* \*